(12) United States Patent
Morris et al.

(10) Patent No.: US 7,780,708 B2
(45) Date of Patent: Aug. 24, 2010

(54) IMPLANT RETAINING DEVICE

(75) Inventors: John W. Morris, Beachwood, NJ (US); Lawrence A. Shimp, Morganville, NJ (US); David R. Kaes, Toms River, NJ (US)

(73) Assignee: Osteotech, Inc., Eatontown, NJ (US)

( * ) Notice: Subject to any disclaimer, the term of this patent is extended or adjusted under 35 U.S.C. 154(b) by 860 days.

(21) Appl. No.: 10/923,392

(22) Filed: Jan. 31, 2005

(65) Prior Publication Data

US 2005/0143740 A1 Jun. 30, 2005

Related U.S. Application Data

(62) Division of application No. 10/032,778, filed on Oct. 22, 2001, now abandoned.

(60) Provisional application No. 60/242,051, filed on Oct. 20, 2000.

(51) Int. Cl.
*A61B 17/70* (2006.01)
*A61B 17/80* (2006.01)

(52) U.S. Cl. .................... 606/279; 606/281

(58) Field of Classification Search ... 623/17.11–17.16; 606/61, 69–71, 246–249, 279–281, 286, 606/298
See application file for complete search history.

(56) References Cited

U.S. PATENT DOCUMENTS

| | | | |
|---|---|---|---|
| 1,025,008 A * | 4/1912 | Miner | ............ 606/71 |
| 2,375,116 A | 5/1945 | Larkin | |
| 2,525,222 A | 10/1950 | Holt | |
| 3,068,916 A | 12/1962 | Richardson | |
| 3,486,505 A | 12/1969 | Morrison | |
| 3,604,298 A | 9/1971 | Dekiel | |
| 3,604,487 A | 9/1971 | Gilbert | |
| 3,703,006 A | 11/1972 | Bokros et al. | |
| 3,848,601 A | 11/1974 | Ma et al. | |
| 4,033,244 A | 7/1977 | Jacobson | |

(Continued)

FOREIGN PATENT DOCUMENTS

AU 744371 11/1998

(Continued)

OTHER PUBLICATIONS

Albee, Fred H., "Bone Surgery with Machine Tools," *Scientific American*, Apr. 1936, pp. 178-181.

(Continued)

*Primary Examiner*—Eduardo C Robert
*Assistant Examiner*—David Comstock
(74) *Attorney, Agent, or Firm*—Kenneth E. Levitt; Dorsey & Whitney LLP

(57) ABSTRACT

There is provided an implant retaining device, which has the effect of preventing an intervertebral implant from jutting out of the receiving bed. The implant retaining device generally includes a plate having at least one throughbore to receive a screw, and a screw for securing the plate to the vertebrae. The plate may be dimensioned to cover a portion of the opening of a receiving bed, and thus, need only be secured to a single vertebral body. In an alternate embodiment, the plate may be used during bone fracture correction procedures to prevent a bone screw from backing out of engagement with adjacent bone sections. A method of retaining an intervertebral implant using the device is also provided.

16 Claims, 2 Drawing Sheets

U.S. PATENT DOCUMENTS

| | | |
|---|---|---|
| 4,059,115 A | 11/1977 | Jumashev et al. |
| 4,185,383 A | 1/1980 | Heimke et al. |
| 4,273,117 A | 6/1981 | Neuhauser |
| 4,349,921 A | 9/1982 | Kuntz |
| 4,394,370 A | 7/1983 | Jefferies |
| 4,416,278 A | 11/1983 | Miller |
| 4,440,750 A | 4/1984 | Glowacki et al. |
| 4,484,570 A | 11/1984 | Sutter et al. |
| 4,485,097 A | 11/1984 | Bell |
| 4,516,276 A | 5/1985 | Mittelmeier et al. |
| 4,553,575 A | 11/1985 | Brown |
| 4,559,936 A | 12/1985 | Hill |
| 4,566,466 A | 1/1986 | Ripple et al. |
| 4,573,448 A | 3/1986 | Kambin |
| 4,637,931 A | 1/1987 | Schmitz |
| 4,649,918 A | 3/1987 | Pegg et al. |
| 4,678,470 A | 7/1987 | Nashef et al. |
| 4,714,469 A | 12/1987 | Kenna |
| 4,743,256 A | 5/1988 | Brantigan |
| 4,743,259 A | 5/1988 | Bolander et al. |
| 4,753,235 A | 6/1988 | Hasson |
| 4,772,287 A | 9/1988 | Ray et al. |
| 4,782,833 A | 11/1988 | Einhorn et al. |
| 4,798,213 A | 1/1989 | Doppelt |
| 4,820,305 A | 4/1989 | Harms et al. |
| 4,834,757 A | 5/1989 | Brantigan |
| 4,863,477 A | 9/1989 | Monson |
| 4,877,020 A | 10/1989 | Vich |
| 4,878,915 A | 11/1989 | Brantigan |
| 4,904,261 A | 2/1990 | Dove et al. |
| 4,917,704 A | 4/1990 | Frey et al. |
| 4,932,973 A | 6/1990 | Gendler |
| 4,938,768 A | 7/1990 | Wu |
| 4,950,296 A | 8/1990 | McIntyre |
| 4,955,885 A | 9/1990 | Meyers |
| 4,961,740 A | 10/1990 | Ray et al. |
| 4,963,154 A | 10/1990 | Anapliotis et al. |
| 4,997,434 A | 3/1991 | Seedhom et al. |
| 5,015,247 A | 5/1991 | Michelson |
| 5,015,255 A | 5/1991 | Kuslich |
| 5,026,373 A | 6/1991 | Ray et al. |
| 5,047,058 A | 9/1991 | Roberts et al. |
| 5,049,150 A | 9/1991 | Cozad |
| 5,053,049 A | 10/1991 | Campbell |
| 5,055,104 A | 10/1991 | Ray |
| 5,061,786 A | 10/1991 | Burnier et al. |
| 5,062,845 A | 11/1991 | Kuslich et al. |
| 5,112,354 A | 5/1992 | Sires |
| 5,171,278 A | 12/1992 | Pisharodi |
| 5,192,321 A | 3/1993 | Strokon |
| 5,192,327 A | 3/1993 | Brantigan |
| 5,197,967 A | 3/1993 | Wilson |
| 5,207,710 A | 5/1993 | Chu et al. |
| 5,236,456 A | 8/1993 | O'Leary et al. |
| 5,284,655 A | 2/1994 | Bogdansky et al. |
| 5,298,254 A | 3/1994 | Prewett et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,312,408 A | 5/1994 | Brown |
| 5,314,476 A | 5/1994 | Prewett et al. |
| 5,314,478 A | 5/1994 | Oka et al. |
| 5,361,483 A | 11/1994 | Rainville et al. |
| 5,380,333 A | 1/1995 | Meloul et al. |
| 5,390,683 A | 2/1995 | Pisharodi |
| 5,397,364 A | 3/1995 | Kozak et al. |
| 5,423,817 A | 6/1995 | Lin |
| 5,425,825 A | 6/1995 | Levine |
| 5,425,772 A | 6/1995 | Brantigan |
| 5,425,773 A | 6/1995 | Boyd et al. |
| 5,439,684 A | 8/1995 | Prewett et al. |
| 5,443,514 A | 8/1995 | Steffee |
| 5,445,639 A | 8/1995 | Kuslich et al. |
| 5,458,638 A | 10/1995 | Kuslich et al. |
| 5,458,643 A | 10/1995 | Oka et al. |
| 5,484,437 A | 1/1996 | Michelson |
| 5,489,307 A | 2/1996 | Kuslich et al. |
| 5,489,308 A | 2/1996 | Kuslich et al. |
| 5,490,962 A | 2/1996 | Cima et al. |
| 5,505,731 A * | 4/1996 | Tornier ........................ 606/61 |
| 5,505,732 A | 4/1996 | Michelson |
| 5,507,813 A | 4/1996 | Dowd et al. |
| 5,514,180 A | 5/1996 | Heggeness et al. |
| 5,518,680 A | 5/1996 | Cima et al. |
| 5,522,899 A | 6/1996 | Michelson |
| 5,534,028 A | 7/1996 | Bao et al. |
| 5,534,030 A | 7/1996 | Navarro et al. |
| 5,545,222 A | 8/1996 | Bonutti |
| 5,554,191 A | 9/1996 | Lahille et al. |
| 5,562,738 A | 10/1996 | Boyd et al. |
| 5,571,190 A | 11/1996 | Ulrich et al. |
| 5,571,192 A | 11/1996 | Schonhoffer |
| 5,591,235 A | 1/1997 | Kuslich |
| 5,593,409 A | 1/1997 | Michelson |
| 5,607,269 A | 3/1997 | Dowd et al. |
| 5,607,424 A | 3/1997 | Tropiano |
| 5,609,635 A | 3/1997 | Michelson |
| 5,609,636 A | 3/1997 | Kohrs et al. |
| 5,632,747 A | 5/1997 | Scarborough et al. |
| 5,645,596 A | 7/1997 | Kim et al. |
| 5,645,598 A | 7/1997 | Brosnahan, III |
| 5,653,761 A | 8/1997 | Pisharodi |
| 5,653,762 A | 8/1997 | Pisharodi et al. |
| 5,653,763 A | 8/1997 | Errico et al. |
| 5,658,336 A | 8/1997 | Pisharodi |
| 5,658,337 A | 8/1997 | Kohrs et al. |
| 5,662,710 A | 9/1997 | Bonutti |
| 5,669,909 A | 9/1997 | Zdeblick et al. |
| 5,683,394 A | 11/1997 | Rinner |
| 5,683,463 A | 11/1997 | Godefroy et al. |
| 5,683,464 A | 11/1997 | Wagner et al. |
| 5,702,391 A | 12/1997 | Lin |
| 5,707,371 A | 1/1998 | Metz-Stavenhagen |
| 5,709,683 A | 1/1998 | Bagby |
| 5,716,415 A | 2/1998 | Steffee |
| 5,716,416 A | 2/1998 | Lin |
| 5,720,751 A | 2/1998 | Jackson |
| 5,728,159 A | 3/1998 | Stroever et al. |
| 5,741,253 A | 4/1998 | Michelson |
| 5,749,916 A | 5/1998 | Richelsoph |
| 5,766,251 A | 6/1998 | Koshino |
| 5,766,252 A | 6/1998 | Henry et al. |
| 5,769,897 A | 6/1998 | Harle |
| 5,776,199 A | 7/1998 | Michelson |
| 5,782,830 A | 7/1998 | Farris |
| 5,782,919 A | 7/1998 | Zdeblick et al. |
| 5,785,710 A | 7/1998 | Michelson |
| 5,800,547 A | 9/1998 | Schafer et al. |
| 5,807,437 A | 9/1998 | Sachs et al. |
| 5,814,084 A | 9/1998 | Grivas et al. |
| 5,824,078 A | 10/1998 | Nelson et al. |
| 5,824,094 A | 10/1998 | Serhan et al. |
| 5,846,484 A | 12/1998 | Scarborough et al. |
| 5,860,973 A | 1/1999 | Michelson |
| 5,865,845 A | 2/1999 | Thalgott |
| 5,868,749 A | 2/1999 | Reed |
| 5,885,299 A | 3/1999 | Winslow et al. |
| 5,885,300 A | 3/1999 | Tokuhashi et al. |
| 5,888,219 A | 3/1999 | Bonutti |
| 5,888,222 A | 3/1999 | Coates |
| 5,888,227 A | 3/1999 | Cottle |
| 5,895,426 A | 4/1999 | Scarborough et al. |
| 5,895,428 A | 4/1999 | Berry |

| | | | | | | |
|---|---|---|---|---|---|---|
| 5,899,939 | A | 5/1999 | Boyce et al. | 2003/0130667 A1 | 7/2003 | Lin |
| 5,904,683 | A * | 5/1999 | Pohndorf et al. ............... 606/61 | 2003/0135214 A1 | 7/2003 | Fetto et al. |
| 5,904,719 | A | 5/1999 | Errico et al. | 2003/0147860 A1 | 8/2003 | Marchosky |
| 5,928,238 | A | 7/1999 | Scarborough et al. | 2004/0024457 A1 | 2/2004 | Boyce et al. |
| 5,941,882 | A | 8/1999 | Jammet et al. | 2004/0044409 A1 | 3/2004 | Alfaro et al. |
| 5,968,047 | A | 10/1999 | Reed | 2004/0098129 A1 | 5/2004 | Lin |
| 5,972,368 | A | 10/1999 | McKay | 2004/0146543 A1 | 7/2004 | Shimp et al. |
| 5,980,522 | A | 11/1999 | Koros et al. | 2004/0243242 A1 | 12/2004 | Sybert et al. |
| 5,984,967 | A | 11/1999 | Zdeblick et al. | 2004/0249377 A1 | 12/2004 | Kaes et al. |
| 5,989,289 | A | 11/1999 | Coates et al. | 2005/0008620 A1 | 1/2005 | Shimp et al. |
| 6,025,538 | A | 2/2000 | Yaccarino, III | 2005/0008672 A1 | 1/2005 | Winterbottom et al. |
| 6,030,635 | A | 2/2000 | Gertzman et al. | 2005/0027033 A1 | 2/2005 | Knaack et al. |
| 6,045,554 | A | 4/2000 | Grooms et al. | 2005/0038511 A1 | 2/2005 | Martz et al. |
| 6,045,579 | A | 4/2000 | Hochshuler et al. | 2005/0107880 A1 | 5/2005 | Shimp et al. |
| 6,045,580 | A | 4/2000 | Scarborough et al. | 2005/0143740 A1 | 6/2005 | Morris et al. |
| 6,066,174 | A | 5/2000 | Farris | 2005/0283255 A1 | 12/2005 | Geremakis et al. |
| 6,077,267 | A | 6/2000 | Huene | 2006/0149376 A1 | 7/2006 | Shimp et al. |
| 6,083,225 | A | 7/2000 | Winslow et al. | 2007/0178158 A1 | 8/2007 | Knaack et al. |
| 6,090,143 | A | 7/2000 | Meriwether et al. | | | |
| 6,096,081 | A | 8/2000 | Grivas et al. | FOREIGN PATENT DOCUMENTS | | |
| 6,102,950 | A | 8/2000 | Vaccaro | | | |
| 6,111,164 | A | 8/2000 | Rainey et al. | DE | 2 253 086 | 10/1972 |
| 6,113,637 | A * | 9/2000 | Gill et al. .................. 623/17.15 | DE | 40 12 622 C | 7/1991 |
| 6,113,638 | A | 9/2000 | Williams et al. | DE | 43 02 397 | 7/1993 |
| 6,123,705 | A | 9/2000 | Michelson | DE | 198 15 407 | 10/1999 |
| 6,123,731 | A | 9/2000 | Boyce et al. | DE | 298 14 174 U | 12/1999 |
| 6,132,472 | A | 10/2000 | Bonutti | EP | 0 302 719 | 2/1989 |
| 6,136,002 | A * | 10/2000 | Shih et al. ..................... 606/61 | EP | 0 307 241 | 3/1989 |
| 6,139,211 | A | 10/2000 | Schroeder et al. | EP | 0 325 566 | 7/1989 |
| 6,143,033 | A | 11/2000 | Paul et al. | EP | 0 332 826 | 9/1989 |
| 6,156,037 | A * | 12/2000 | LeHuec et al. .............. 606/247 | EP | 0 493 698 | 7/1992 |
| 6,159,215 | A | 12/2000 | Urbahns et al. | EP | 0 732 093 | 2/1996 |
| 6,174,311 | B1 | 1/2001 | Branch et al. | EP | 0 734 703 | 10/1996 |
| 6,200,347 | B1 | 3/2001 | Anderson et al. | EP | 1 064 890 | 1/2001 |
| 6,206,923 | B1 | 3/2001 | Boyd et al. | FR | 2636227 | 3/1990 |
| 6,210,442 | B1 | 4/2001 | Wing et al. | FR | 2703580 | 10/1994 |
| 6,235,059 | B1 | 5/2001 | Benezech et al. | FR | 2742652 | 6/1997 |
| 6,258,125 | B1 | 7/2001 | Paul et al. | FR | 2769827 | 4/1999 |
| 6,270,528 | B1 | 8/2001 | McKay | JP | 01/179689 | 7/1989 |
| 6,277,149 | B1 * | 8/2001 | Boyle et al. ............... 623/17.16 | SU | 1107854 | 8/1984 |
| 6,294,041 | B1 | 9/2001 | Boyce et al. | SU | 590872 A | 11/1985 |
| 6,294,187 | B1 * | 9/2001 | Boyce et al. ................. 424/422 | WO | WO 89/09035 | 10/1989 |
| 6,315,795 | B1 | 11/2001 | Scarborough et al. | WO | WO 93/01771 | 2/1993 |
| 6,326,018 | B1 | 12/2001 | Gertzman et al. | WO | WO 94/21298 | 9/1994 |
| 6,350,283 | B1 * | 2/2002 | Michelson ............... 623/17.11 | WO | WO 97/15246 | 5/1997 |
| 6,379,385 | B1 | 4/2002 | Kalas et al. | WO | WO 97/47258 | 12/1997 |
| 6,383,221 | B1 | 5/2002 | Scarborough et al. | WO | WO 98/02117 | 1/1998 |
| 6,425,920 | B1 | 7/2002 | Hamada | WO | WO 98/48738 | 11/1998 |
| 6,432,107 | B1 | 8/2002 | Ferree | WO | WO 99/07312 | 2/1999 |
| 6,454,806 | B1 | 9/2002 | Cohen et al. | WO | WO 99/09914 | 3/1999 |
| 6,468,543 | B1 | 10/2002 | Gilbertson et al. | WO | WO 99/21515 | 5/1999 |
| 6,527,773 | B1 | 3/2003 | Lin et al. | WO | WO 99/38461 | 8/1999 |
| 6,530,955 | B2 | 3/2003 | Boyle et al. | WO | WO 00/07527 | 2/2000 |
| 6,547,823 | B2 | 4/2003 | Scarborough et al. | WO | WO 00/24327 | 5/2000 |
| 6,569,168 | B2 | 5/2003 | Lin | WO | WO 00/40177 | 7/2000 |
| 6,579,321 | B1 | 6/2003 | Gordon et al. | WO | WO 00/40179 | 7/2000 |
| 6,638,310 | B2 | 10/2003 | Lin et al. | WO | WO 01/00792 | 1/2001 |
| 6,696,073 | B2 | 2/2004 | Boyce et al. | WO | WO 01/49220 | 7/2001 |
| 6,733,504 | B2 | 5/2004 | Lin et al. | WO | WO 01/66048 | 9/2001 |
| 6,855,167 | B2 | 2/2005 | Shimp et al. | WO | WO 01/70136 | 9/2001 |
| 6,863,694 | B1 * | 3/2005 | Boyce et al. .............. 623/23.63 | WO | WO 01/70137 | 9/2001 |
| 6,911,045 | B2 | 6/2005 | Shimp | WO | WO 01/70139 | 9/2001 |
| 2001/0020186 | A1 | 9/2001 | Boyce et al. | WO | WO 01/78798 | 10/2001 |
| 2001/0043258 | A1 | 11/2001 | Ohki | WO | WO 03/030956 A2 | 4/2003 |
| 2002/0029084 | A1 | 3/2002 | Paul et al. | WO | WO 2005/072656 | 8/2005 |
| 2002/0045897 | A1 * | 4/2002 | Dixon et al. .................. 606/61 | | | |
| 2002/0058950 | A1 | 5/2002 | Winterbottom et al. | | | |
| 2002/0128717 | A1 | 9/2002 | Alfaro et al. | OTHER PUBLICATIONS | | |
| 2002/0161445 | A1 | 10/2002 | Crozel | | | |
| 2002/0188295 | A1 | 12/2002 | Martz et al. | *Allograft Freeze-Dried Release Specifications,* Osteotech, Inc., Sep. 30, 1992, 3 pages. | | |
| 2003/0039676 | A1 | 2/2003 | Boyce et al. | | | |
| 2003/0049326 | A1 | 3/2003 | Nimni | Brantigan, J.W., DePuy AcroMed, Lumbar I/F Cage With VSP Spinal System (Surgical Technique) (1999). | | |
| 2003/0060825 | A1 | 3/2003 | Alfaro et al. | | | |

Crowe et al., "Inhibition of Enzymatic Digestion of Amylose by Free Fatty Acids in Vitro Contributes to Resistant Starch Formation", J. Nutr. 130(8): 2006-2008, 2000.

DePuy AcroMed, Lumbar I/F Cage Implants & Instruments (Product Catalog) (1999).

Driessens et al., "Calcium phosphate bone cements," *Universitat Politecnica de Catalunya,* Barcelona, Spain, 31: 855-77.

Edwards et al., "Osteoinduction of Human Demineralized Bone: Characterization in Rat Model", Clinical Orthopaedics and Related Research, No. 357, pp. 219-228 (1998).

Frymoyer et al., Eds., "The Adult Spine Principles and Practice," *Poster Lumbar Interbody Fusion,* James W. Simmons, vol. 2, pp. 1961-1987 (1991).

Gerhart et al. "Biomechanical optimization of a model particulate composite for orthopaedic applications," *J. Orthop. Res* (1986); 4(1): 86-85 [abstract only].

Glowacki et al., "Fate of Mineralized and Demineralized Osseous Implants in Cranial Defects", Calcified Tissue Int. 33: 71-76, 1981.

Glowacki et al., "Demineralized Bone Implants", Symposium on Horizons in Plastic Surgery, vol. 12, No. 2, pp. 233-241 (1985).

Han et al. "Quantitative and sensitive in vitro assay for osteoinductive activity of demineralized bone matrix," J. Orthop. Res., 21(4): 648-54, 2003.

Jain et al., "Anchoring of phospholipase A2: the effect of anions and deuterated water, and the role of N-terminus region," *Biochem. et Biophys. Acta,* 860:448-61, 1986.

Katz, "The biology of heavy water," *Scientific American,* 106-116, 1960.

Lewandrowski et al., "Improved Osteoinduction of Cortical Bone Allografts: A Study of the Effects of Laser Perforation and Partial Demineralization," *J. Ortho Res.* 15:748-756 (1997).

Ma, G.W.C., Posterior Lumbar Interbody Fusion with Specialized Instruments, *Clinical Ortho and Rel. Res.,* 193 (March) pp. 57-63 (1985).

McCord et al., "Anterior endoscopic thoracolumbar instrumentation and implants," *Curr. Ortho 12,* pp. 96-103 (1998).

MTF Bone Catalog, Fibular Wedges, Femoral Struts, Tibial Struts, published prior to 2000, 1 page.

Neigal et al., "Use of Demineralized Bone Implants in Orbital and Craniofacial", Opthal. Plast. Reconstrs. Surg., 12: 108-120, 1996.

Ray et al., "Preliminary Report of an Experimental Study", J. Bone Joint Surgery, 39 A: 1119-1128, 1957.

Russell et al., "Clinical Utility of Demineralized Bone Matrix for Osseous Defects, Arthrodesis and Reconstruction: Impact of Processing Techniques and Study Methodology", Orthpaedics, 22(5): 524-531, 1999.

Smith, MD et al. "Load-bearing capacity of corticocancellous bone grafts in the spine" (truncated abstract), Aug. 1993, *Journal of Bone & Joint Surgery,* 75(8): 1206-13.

Sofamar Danek, "Surgical Technique Using Bone Dowel Instrumentation for Anterior Approach" [Publication Date Unknown].

Stevenson, S., "Enhancement of Fracture Healing with Autogenous and Allogeneic Bone Grafts," *Clin. Ortho, Rel. Res.* 355S, pp. S239-S246 (1998).

Tan et al., A modified technique of anterior Lumbar fusion with femoral cortical allograft; *J. Orthop. Surg. Tech;* vol. 5, No. 3 1990), pp. 83-93, 1990.

Ueland et al., "Increased Cortical Bone Content of Insulin-Like Growth Factors in Acromegalic Patients", J. Clin. Endocrinol. Metab., 84(1): 123-127, 1999.

University of Florida Tissue Bank, Inc., Allograft Catalog [Publication Date Unknown].

University of Florida Tissue Transplant Patient Education Series [Publication Data Unknown].

Urist et al., "Observations implicating an extracellular enzymic mechanism of control of bone morphogenesis," *J. Histochem & Cytochem,* 22(2): 88-103, 1974.

Urist et al., "Preservation and biodegradation of the morphogenetic property of bone matrix," *J. Theor. Biol.* 38: 155-67, 1973.

Urist, "Bone: Formation by Autoinduction", Science, 150: 893-899, 1965.

VG2 Interbody Bone Grafts, DuPuy AcroMed, 2000, 6 pages.

Vich, Jose M. Otero, "Anterior cervical interbody fusion with threaded cylindrical bone," J. Neurosurg. 63:750-753, 1985.

Whiteman et al., "Demineralized Bone Powder—Clinical Applications for Bone Defects of the Hand", J. Hand. Surg., 18B: 487-490, 1993.

Whittaker et al., "Matrix Metalloproteinases and Their Inhibitors—Current Status and Future Challenges", Celltransmissions, 17(1): 3-14.

Xiabo et al., "Experimental and Clinical Investigations of Human Insoluble Bone Matrix Gelatin", Clin. Orthrop. 293: 360-365, 1993.

Zhang, et al., "A Quantative Assessment of Osteoinductivity of Human Demineralized Bone Matrix", J. Periodontol. 68(11): 1076-1084, 1997.

\* cited by examiner

IMPLANT RETAINING DEVICE

CROSS REFERENCE TO RELATED APPLICATIONS

This application is a divisional of prior filed U.S. patent application Ser. No. 10/032,778, filed Oct. 22, 2001, now abandoned, and claims priority to U.S. Provisional Application Ser. No. 60/242,051 filed Oct. 20, 2000, the contents of which are hereby incorporated by reference.

BACKGROUND OF THE INVENTION

1. Technical Field

The present disclosure is directed to an implant retaining device for preventing an implant from backing out of a receiving bed or graft site formed in body tissue. More specifically, the present disclosure is directed to an implant retaining device particularly suited for retaining an intervertebral implant in a receiving bed formed between adjacent vertebrae.

2. Background of Related Art

The spine is a flexible column formed of a series of bone called vertebrae. The vertebrae are hollow and piled one upon the other, forming a strong hollow column for support of the cranium and trunk. The hollow core of the spine houses and protects the nerves of the spinal cord. The vertebrae are connected together by means of articular processes and intervertebral, fibro-cartilages.

The intervertebral fibro-cartilages are also known as intervertebral disks and are made of a fibrous ring filled with pulpy material. The disks function as spinal shock absorbers and also cooperate with synovial joints to facilitate movement and maintain flexibility of the spine. When one or more disks degenerate through trauma, spondylolisthesis or other pathologies, nerves passing near the affected area may be compressed and are consequently irritated. The result may be chronic and/or debilitating back pain. Various methods and apparatus, both surgical and non-surgical, have been designed to relieve such back pain.

One method designed to relieve such back pain is interbody spinal fusion. Typically, interbody spinal fusion involves distracting adjoining vertebrae of the spine so that the nerve root canal sizes are increased and nerve irritation is eliminated or reduced. In order to maintain the adjoining vertebrae in a distracted state, at least one intervertebral implant is inserted into a receiving bed formed in the disk space between the adjoining vertebrae. The implant is positioned to engage the adjoining vertebrae to maintain the vertebrae at a fixed degree of distraction.

Preferably, the implant should become fused to adjoining vertebrae in order to prevent the implant and adjoining vertebrae from moving. The implant must also provide spinal load support between the vertebrae. Further, during the time it takes for fusion, i.e., biological fixation of the vertebrae, to be completed, the implant should have enough structural integrity to maintain the disk space without substantial degradation or deformation of the implant.

To facilitate rapid bone growth, the implant may include or be provided with a bone growth material. The material from which the implant is constructed should be a biocompatible material and, preferably, interact biologically with the body's own naturally occurring tissues.

In order to have successful spinal fusion and maintain the stability of the spine, the vertebral implant must be fixedly positioned in relation to the adjoining vertebrae during the entire period required for fusion to occur. However, the every-day activity of a patient who has undergone a spinal fusion procedure may lead to progressive mechanical loosening and eventual failure of the implant. This significantly decreases the chances of obtaining successful fusion of the implant and the adjoining vertebrae. Therefore, it is imperative that the implant be fixedly retained in the intervertebral space during the period required for spinal fusion.

A variety of different devices have been developed to retain an intervertebral implant at a fixed position within the intervertebral space. These devices include, inter alia, screws and formations formed on the implant itself. Such devices often inhibit insertion of the implant into the intervertebral space.

Accordingly, a need exists for an improved implant retaining device which is configured to reduce the likelihood of expulsion or retropulsion of an intervertebral implant from between adjoining vertebrae during normal patient activity, without inhibiting insertion of the implant into the intervertebral space.

SUMMARY

In accordance with the present disclosure, an implant retaining device is provided which prevents expulsion of an intervertebral implant from an intervertebral receiving bed. In one embodiment the implant retaining device includes a plate having at least one throughbore dimensioned to receive a screw. Single or multiple screws can be used to secure the plate to the vertebrae. The plate may have a rectangular, circular, or any other configuration capable of performing the intended function of preventing expulsion of an intervertebral implant from the receiving bed.

The plate can be secured to one or both vertebral bodies to prevent the intervertebral implant from backing out of the receiving bed. The plate may be dimensioned to cover a portion of the opening of a receiving bed, and thus, need only be secured to a single vertebral body. Alternately, the plate may be dimensioned to extend entirely across the disc space and may be secured to one or both of the vertebral bodies.

When the plate is formed from bone, it may be partially or fully demineralized. Partially demineralized bone provides a degree of flexibility to the plate such that it can be manipulated to conform to the surface to which it is secured, e.g., the vertebrae. Demineralization also improves the osteoconductive and osteoconductive characteristics of the plate.

In an alternate embodiment, the plate may be used in surgical procedures other than spinal interbody fusion procedures. For example, the plate may be used during bone fracture correction procedures to prevent a bone screw from backing out of engagement with adjacent bone sections.

Also disclosed herein is a method of retaining an intervertebral implant in a receiving bed using the disclosed implant retaining device. The method includes attaching a plate, dimensioned to cover at least a portion of the receiving bed, to a vertebral body and securing the upper portion of the plate to the vertebral body utilizing at least one screw. Alternately, the method includes attaching a plate to adjacent vertebral bodies using at least two screws.

BRIEF DESCRIPTION OF THE DRAWINGS

Various preferred embodiments of the presently disclosed implant retaining device are described herein with reference to the drawings wherein.

DETAILED DESCRIPTION OF PREFERRED EMBODIMENTS

Figure 1A:
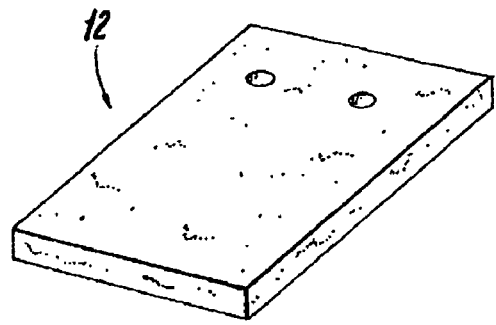
FIG. 1A is a perspective view of one preferred embodiment of the presently disclosed implant retaining device having a rectangular configuration.

Preferred embodiments of the presently disclosed implant retaining device will now be described in detail with reference to the drawings in which like reference numerals designate identical or corresponding elements in each of the several views.

The implant retaining device of the present invention is intended to be attached to at least one vertebral body, to cover at least a portion of the disk space to prevent a vertebral implant from backing out of a receiving bed. The implant retaining device is especially suited for procedures where it would be desirable to prevent an implant from backing out of the spine. However, it is entirely suitable to applications involving the repair of other bony sites in the body.

In humans, the device may be used predominately in the lumbar and thoracic regions of the spine, but, is adaptable for use in the cervical spine and other regions of the body as well.

The implant retaining device described herein may be formed of any biocompatible material or combination of materials. "Biocompatible" means that no serious systemic toxicity is caused by the presence of the material in a living system. It is contemplated that biocompatible materials may cause some clinically acceptable amounts of toxicity including irritation and/or other adverse reactions in certain individuals. For example, the material described in U.S. Pat. No. 5,899,939, the contents of which are incorporated herein by reference, may be entirely suitable for fabricating all or a portion of the implant retaining device described herein.

The implant retaining device may also be fabricated from any of the various biocompatible polymers. Examples of biocompatible polymers suitable for use herein would include bioabsorbable polymeric materials such as, for example, polymers and/or copolymers containing any of the following polymerizable monomers: epsilon-caprolactone, glycolide, trimethylene carbonates, tetramethylene carbonates, dimethyl trimethylene carbonates; dioxanones; diox-epanones; absorbable cyclic amides; absorbable cyclic ether-esters derived from crown ethers; hydroxyacids capable of esterification, including both alpha hydroxyacids (such as glycolic acid and lactic acid) and beta hydroxyacids (such as beta hydroxybutyric acid and gamma hydroxyvaleric acid); polyalkyl ethers (such as polyethylene glycol and polypropylene glycol and combinations thereof), etc. Of course non-bioabsorbable polymers that are biocompatible such as, for example, polytetrafluoroethylene, would also be suitable for fabricating any or all of the components of the implant retaining device described herein.

The implant retaining device may also be fabricated from metallic materials commonly used in the fabrication of implantable devices, for example, surgical stainless steel, titanium, titanium alloys, etc. Ceramic materials such as, hydroxyapatite, bioglass, etc., may also be used for the fabrication of the device described herein. Of course, any combination of materials may be used to fabricate the entire implant retaining device described herein as well as the various components of the fixation system herein. Any and all such combinations of biocompatible materials are envisioned as being within the scope of the disclosure herein.

Figure 1B:
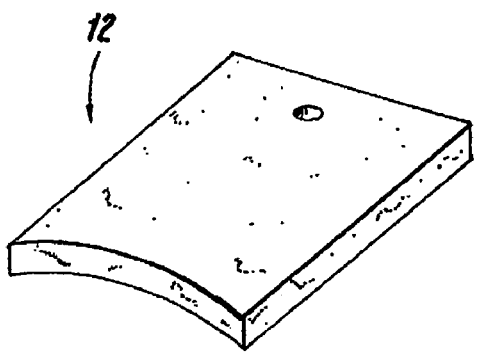
FIG. 1B is a perspective view of another preferred embodiment of the presently disclosed implant retaining device having a rectangular configuration and a curvature along its transverse axis.
Figure 1C:
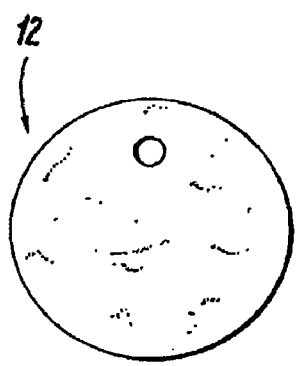
FIG. 1C is a top view of another preferred embodiment of the presently disclosed implant retaining device having a circular configuration.
Figure 1D:
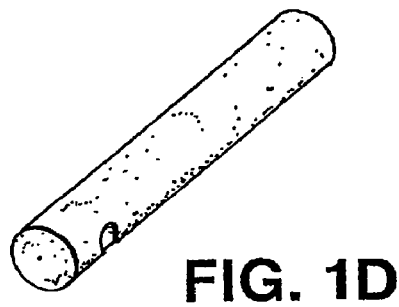
FIG. 1D is a perspective view of another preferred embodiment of the presently disclosed implant retaining device having a rod shaped configuration.
Figure 2:
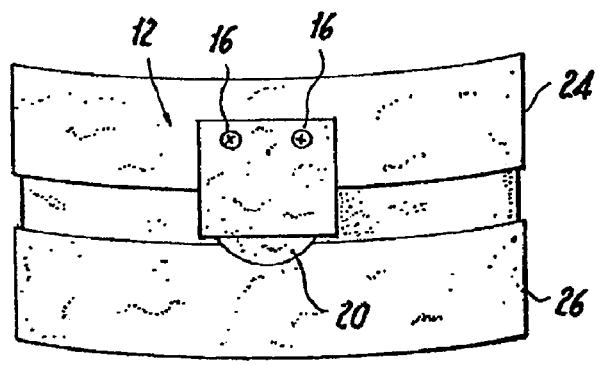
FIG. 2 is a front view of the implant retaining device shown in FIG. 1A secured to a vertebral body with a pair of screws.
Figure 3:
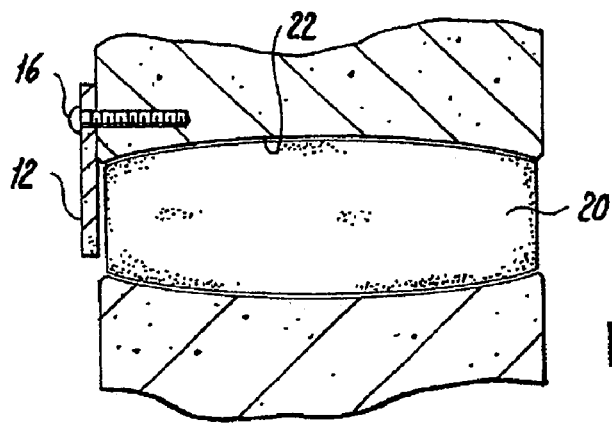
FIG. 3 is a side view of the implant retaining device shown in FIG. 1A secured to a vertebral body with a bone screw to retain a concave implant between adjacent vertebral bodies.
Figure 4:
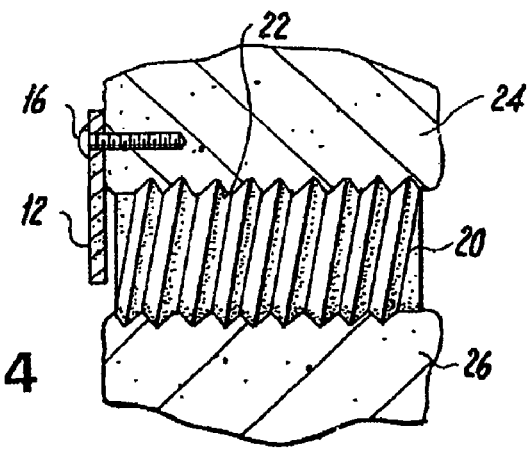
FIG. 4 is a side view of the implant retaining device shown FIG. 1A secured to a vertebral body with a bone screw to retain a cylindrical dowel between adjacent vertebral bodies.

Referring to FIGS. 1A-D, implant retaining device 10 includes a plate 12 having at least one throughbore 14 dimensioned to receive a screw 16 (see FIGS. 2-4). Plate 12 may vary in thickness depending on the size and shape of the vertebral body and the vertebral implant with which the plate 12 is being utilized. The thickness of plate 12 may also vary depending on whether the implant retaining device is adapted for use in the lumbar, thoracic or cervical spinal regions, or other regions of the body. The thickness of plate 12 may vary from at least about 0.5 mm to about 1.0 cm. Preferably, plate 12 is between about 2 mm to about 5 mm. Plate 12 can be formed from any biocompatible material having the requisite strength requirements including, as discussed above, cancellous or cortical bone, ceramics, polymers, composites, etc. Preferably, plate 12 is constructed from cortical bone. Plate 12 may have a rectangular configuration (FIG. 1A), a circular configuration (FIG. 1C), a rod shaped configuration (FIG. 1D), or any other configuration capable of performing the intended function described herein. Plate 12 may also be provided with a curvature along its longitudinal and/or transverse axis (FIG. 1B). The curvature may be selected to correspond to the curvature of a surface against which plate 12 is to be secured, e.g., a vertebrae.

Referring to FIGS. 2-4, plate 12 is suitable for use in preventing an intervertebral implant 20 from backing out of a receiving bed 22 formed between adjacent vertebral bodies 24 and 26 during a spinal interbody fusion procedure. Intervertebral implants include cylindrical dowels (FIG. 4), wedge-shaped implants, rectangular spacers, concave or convex implants (FIG. 3), etc. During an intervertebral implantation procedure, the intervertebral implant 20 is placed between adjacent vertebral bodies to support the vertebral bodies at a desired orientation and spacing to facilitate spinal fusion. Such procedures are well known in the art and will not be discussed in further detail herein.

After intervertebral implant 20 has been placed between vertebral bodies 24 and 26, plate 12 can be secured to one or both of the vertebral bodies 24 and 26 to prevent implant 20 from backing out of receiving bed 22. As illustrated, plate 12 need only be dimensioned to cover a portion of the opening of receiving bed 22, and thus, need only be secured to a single vertebral body. To minimize damage to the vertebral bodies, attachment to a single vertebral body is preferred. Alternately, plate 12 may be dimensioned to extend entirely across the disc space and may be secured to one or both of the vertebral bodies (not shown).

When plate 12 is formed from bone, it may be partially or fully demineralized using, for example, a controlled acid treatment. Plate 12 may be partially demineralized to provide a degree of flexibility to the plate such that it can be manipulated to conform to the surface to which it is secured, e.g., the vertebrae. Alternately, plate 12 may be partially demineralized to increase the osteoinductive characteristics of the plate. For example, the surface of the plate to be secured adjacent to a vertebral surface may be surface demineralized to promote osteogenic growth.

Figure 5:
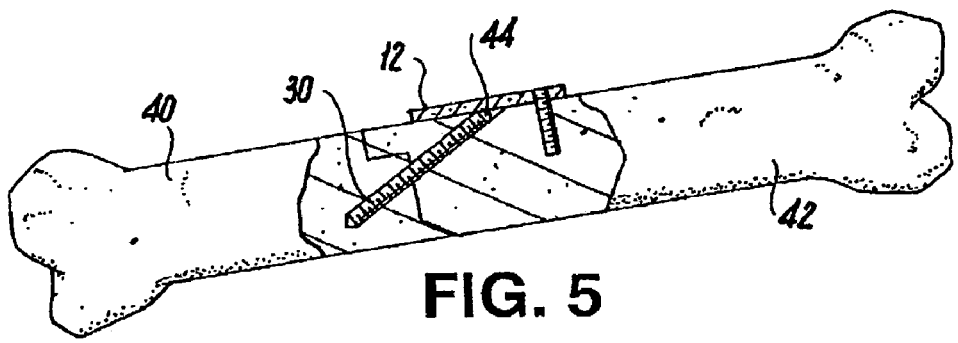
FIG. 5 is a side view of the implant retaining device shown in FIG. 1A utilized in a bone fracture correction procedure to prevent a bone screw from backing out of engagement with adjacent bone sections.

In an alternate embodiment, plate 12 may be used in surgical procedures other than spinal interbody fusion procedures. For example, plate 12 may be used to prevent a bone screw 30 from backing out of engagement with adjacent bone sections during bone fracture correction procedures. See FIG. 5. In such a procedure, after the bone screw has been screwed into the bone sections 40 and 42, plate 12 can be affixed over the head 44 of the bone screw 30 to prevent the bone screw 30 from backing out of the insertion bore. As illustrated, a single screw 16 can be used to secure plate 12 to the bone section 42. Alternately, multiple screws can be used to secure plate 12 to bone section 42, or bone sections 40 and 42, e.g., one screw at each end of plate 12.

The screw 16 and/or bone screw 30 can be formed from any biocompatible material having the requisite strength requirements including surgical grade metals, cancellous or cortical bone, bone composites, polymers, BMP's, etc. Preferably, screws 16 and 30 are formed from cortical bone such as disclosed in U.S. application Ser. No. 09/542,556, issued as U.S. Pat. No. 6,368,322 on Apr. 9, 2002, the entirety of which is hereby incorporated by reference.

A method of using the implant retaining device is also described herein. In use, plate 12 is attached to one or more vertebral bodies 24 and 26 to prevent an intervertebral implant from backing out of an intervertebral receiving bed. The plate is dimensioned to cover at least a portion of the opening to the receiving bed and may extend over the entire receiving bed opening. Thereafter, the plate may be secured to one or both of the vertebral bodies using a bone screw or screws. Alternately, other fastening techniques may be used to secure the plate to the vertebral body or bodies, e.g., nails, adhesives, pins, etc.

Figure 6:
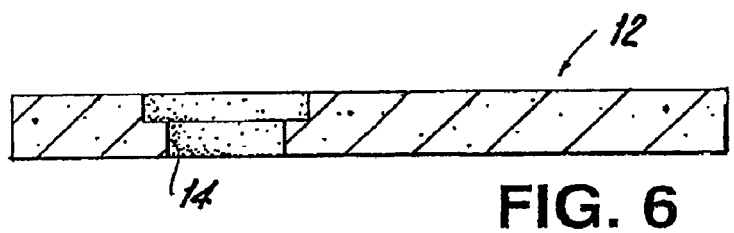
FIG. 6 is a cross-sectional view of another embodiment of the presently disclosed implant retaining device having a stepped bore configured to receive the head of a bone screw.

It will be understood that various modifications may be made to the embodiments disclosed herein. For example, the plate 12 may be constructed having a variety of configurations other than those illustrated herein including rectangular, triangular, etc. Moreover, multiple plates may be used simultaneously, i.e., one plate may extend from each side of the graft site. Further, the plate may include a stepped bore 15 formed about throughbore 14 to receive the head 17 of the screw 16. See FIG. 6. Therefore, the above description should not be construed as limiting, but merely as exemplifications of preferred embodiments. Those skilled in the art will envision other modifications within the scope and spirit of the claims appended hereto.

What is claimed is:

1. A method of retaining an intervertebral implant within a receiving bed formed between adjoining vertebral bodies, the method comprising the following steps:

placing the intervertebral implant between the adjoining vertebral bodies;

providing a retaining plate, separate from the intervertebral implant, the retaining plate having a least one throughbore for receiving a bone screw, the retaining plate being dimensioned to extend at least partly across a disk space defined between the adjoining vertebral bodies, and attaching the retaining plate to one of the adjoining vertebral bodies and leaving the retaining plate unattached to the other of the adjoining vertebral bodies, such that the retaining plate extends at least partly across the disk space between the vertebral bodies and is positioned substantially outside of the disk space, and such that, following implant of the retaining plate, the retaining plate remains in a non-connecting relationship with the intervertebral implant and the other of the adjoining vertebral bodies.

2. The method as recited in claim 1, wherein said plate has a rectangular configuration.

3. The method as recited in claim 1, wherein said plate has a circular configuration.

4. The method as recited in claim 1, wherein said plate is curved along its longitudinal axis.

5. The method as recited in claim 1, wherein said plate is curved along its transverse axis.

6. The method as recited in claim 1, wherein said plate is formed from bone.

7. The method as recited in claim 6, wherein the bone is cortical bone.

8. The method as recited in claim 6, wherein the bone is partially demineralized bone.

9. A method of retaining an intervertebral implant within a receiving bed formed between adjoining vertebral bodies, the method comprising the following steps:

placing the intervertebral implant between the adjoining vertebral bodies;

providing a retaining plate, separate from the intervertebral implant, the retaining plate having at least one throughbore for receiving a bone screw, the retaining plate being dimensioned to extend from one of the adjoining vertebral bodies generally partially across a disk space defined between the adjoining vertebral bodies, and configured for attachment through the at least one throughbore to one of the adjoining vertebral bodies and remain free relative the other of the adjoining vertebral bodies following implant of the retaining plate; and attaching the retaining plate to the one of the adjoining vertebral bodies such that the retaining plate extends generally partially across the disk space between the vertebral bodies and is positioned substantially outside of the disk space.

10. The method as recited in claim 9, wherein said plate has a rectangular configuration.

11. The method as recited in claim 9, wherein said plate has a circular configuration.

12. The method as recited in claim 9, wherein said plate is curved along its longitudinal axis.

13. The method as recited in claim 9, wherein said plate is curved along its transverse axis.

14. The method as recited in claim 9, wherein said plate is formed from bone.

15. The method as recited in claim 14, wherein the bone is cortical bone.

16. The method as recited in claim 14, wherein the bone is partially demineralized bone.

* * * * *